United States Patent
Kobayashi et al.

(10) Patent No.: US 12,228,582 B2
(45) Date of Patent: Feb. 18, 2025

(54) METHOD AND APPARATUS FOR TESTING NEAR INFRARED-PHOTOIMMUNOTHERAPY TREATMENT

(71) Applicants: SHIMADZU CORPORATION, Kyoto (JP); THE UNITED STATES OF AMERICA, as represented by THE SECRETARY, DEPARTMENT OF HEALTH AND HUMAN SERVICES, Bethesda, MD (US)

(72) Inventors: Hisataka Kobayashi, Bethesda, MD (US); Masayuki Nishimura, Columbia, MD (US)

(73) Assignees: SHIMADZU CORPORATION, Kyoto (JP); The United States of America as Represented By The Secretary of the Department of Health and Human, Bethesda, MD (US)

( * ) Notice: Subject to any disclaimer, the term of this patent is extended or adjusted under 35 U.S.C. 154(b) by 939 days.

(21) Appl. No.: 17/253,671

(22) PCT Filed: Jun. 20, 2019

(86) PCT No.: PCT/US2019/038097
§ 371 (c)(1),
(2) Date: Dec. 18, 2020

(87) PCT Pub. No.: WO2019/246322
PCT Pub. Date: Dec. 26, 2019

(65) Prior Publication Data
US 2021/0263054 A1 Aug. 26, 2021

Related U.S. Application Data

(60) Provisional application No. 62/688,031, filed on Jun. 21, 2018.

(51) Int. Cl.
| | | |
|---|---|---|
| G01N 33/94 | (2006.01) | |
| A61K 41/00 | (2020.01) | |
| A61K 47/68 | (2017.01) | |
| C07K 16/28 | (2006.01) | |
| G01N 33/68 | (2006.01) | |

(52) U.S. Cl.
CPC ......... *G01N 33/94* (2013.01); *A61K 41/0042* (2013.01); *A61K 41/0071* (2013.01); *A61K 47/6849* (2017.08); *A61K 47/6855* (2017.08); *C07K 16/2863* (2013.01); *G01N 33/6848* (2013.01)

(58) Field of Classification Search
None
See application file for complete search history.

(56) References Cited

U.S. PATENT DOCUMENTS

| | | |
|---|---|---|
| 2012/0010558 A1 | 1/2012 | Kobayashi et al. |
| 2013/0336995 A1 | 12/2013 | Kobayashi et al. |
| 2014/0120199 A1 | 5/2014 | Terasaki et al. |
| 2016/0001589 A1 | 1/2016 | Zimdahl et al. |
| 2017/0122853 A1 | 5/2017 | Kobayashi et al. |

FOREIGN PATENT DOCUMENTS

| | | |
|---|---|---|
| JP | 2007-537972 A | 12/2007 |
| JP | 2017-524002 A | 8/2017 |
| WO | 2004106385 A2 | 12/2004 |
| WO | 2016/022896 A1 | 2/2016 |

OTHER PUBLICATIONS

Pang et al., Evidence-based complementary and Alternative Medicine 2016: 1-7 (Year: 2016).*
Lloyd et al. Protein Engineering, Design & Selection 22: 159-168 (Year: 2009).*
Edwards et al., J Mol Biol. 334(1): 103-118 (Year: 2003).*
Stillwell, WG et al., Urinary Excretion of Unmetabolized and Phase II Conjugates of 2-Amino-1-methyl 6-phenylimidazo[4,5-b]pyridine and 2-Amino-3,8-dimethylimidazo [4,5-f] quinoxaline in Humans: Relationship to Cytochrome P45OiA2 and N-Acetyltransferase Activity, Cancer Research. Aug. 15, 1997; vol. 57, No. 16; pp. 3457-3464.
Sato, K et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy", ACS Central Science. Nov. 6, 2018; vol. 4, No. 11; pp. 1559-1569.
International Search Report of PCT/US2019/038097 dated Oct. 10, 2019 [PCT/ISA/210].
Written Opinion of PCT/US2019/038097 dated Oct. 10, 2019 [PCT/ISA/237].

(Continued)

*Primary Examiner* — Phuong Huynh
(74) *Attorney, Agent, or Firm* — Sughrue Mion, PLLC

(57) ABSTRACT

A method and treatment for testing efficiency and effectiveness of a near infrared photoimmunotherapy treatment includes injecting an antibody photosensitizer conjugate (APC) into a patient, applying radiation to the patient, thereby causing the APC to release a ligand, which is excreted in the patient's urine, detecting the presence of the ligand with liquid chromatography-mass spectrometry, measuring and quantifying an amount of the ligand present in the patient's urine based on analytical results of the liquid chromatography-mass spectrometry, and determining the effectiveness of the near infrared photo-immunotherapy treatment based on the measured quantified amount of the ligand present in the patient's urine so as to determine an amount of APC remaining in the patient.

8 Claims, 6 Drawing Sheets

(56) References Cited

OTHER PUBLICATIONS

Communication dated Mar. 22, 2022 from the Japanese Patent Office in Application No. 2021-520095.
Japanese Office Action dated May 21, 2024 in Application No. 2023-030862.
Japanese Office Action dated May 21, 2024 in Application No. 2021-520095.
Japanese Office Action dated Nov. 21, 2023 in Japanese Application No. 2021-520095.

* cited by examiner

Mitsunaga et al., Nat Med. 17(12): 1685-1691.
Cancer Cell-Selective in Vivo Near Infrared Photoimmunotherapy Targeting Specific Membrane Molecules

| | |
|---|---|
| Instruments: | Nexera LCMS-8050 system |
| | |
| Flow rate: | 0.4 mL/min |
| Mobile phase: | 20mM Ammonium formate aq (A), Acetonitrile (B) |
| Time program: | 1% (0.0 min) - 40%B (5.0 min) - 98%B (5.1 - 7.0 min)  1%B (7 1 min  10 min) |
| Inj. Vol.: | 1 μL |
| Column oven: | 40 °C |
| Column: | Imtakt Scherzo SM-C18 (2x150 mm, 3 μm) |
| | |
| Neb gas flow: | 2 L/min |
| Heating gas flow: | 10 L/min |
| Interface temp: | 300 °C |
| DL Temperature: | 250 °C |
| Heat block temp | 400 °C |
| MRM transitions: | 500.00>458.00 |
| | 500.00<440.00 |
| | 500.00>197.00 |
| | 500.00>75.10 (Quantitative ion) |

FIG. 5

METHOD AND APPARATUS FOR TESTING NEAR INFRARED-PHOTOIMMUNOTHERAPY TREATMENT

CROSS-REFERENCE TO RELATED APPLICATION

This application is a National Stage of International Application No. PCT/US2019/038097, filed Jun. 20, 2019, claiming priority from U.S. Provisional Application No. 62/688,031, filed on Jun. 21, 2018, filed in the United States Patent & Trademark Office, the disclosure of which are incorporated herein by reference in its entirety.

BACKGROUND

Methods, apparatuses, and treatments consistent with embodiments relate to near infrared photo-immunotherapy.

Patients having aggressive human cancers such as mesothelioma, pancreatic cancer, ovarian cancer, etc., are oftentimes unresponsive to surgery, chemotherapy, radiation therapy, or other traditional cancer therapies, making treatment of the caner problematic.

Near Infrared-Photoimmunotherapy (NIR-PIT) is a revolutionary cancer therapy treatment that uses near-infrared light to rapidly and selectively destroy cancer cells. This cancer therapy treatment has been developed to treat cancers that may be unresponsive to the traditional treatments described above. See, for example, U.S. Patent Application Publications 2017/0122853, 2016/001589, 2014/0120199, US 2013/0336995, and 2012/0010558 to Kobayashi et al., which are incorporated, in their entirety by-reference herein.

Presently, NIR-PIT allows for the human immune system to actively destroy cancerous tumors by depleting the tumor microenvironment of certain cells that act to restrain the immune response.

In NIR-PIT treatment, an antibody, which targets cancerous cells is joined to a photoabsorber/photosensitizer, such as a phthalocyanine dye, e.g., IRDye® 700DX, so as to form an antibody photosensitizer conjugate (APC). This APC is injected into a patient, wherein the APC travels through the blood stream to reach a tumor containing cancerous cells. The conjugate then leaks out from permeable vessels near the tumor. The conjugate then binds to an antigen, a cell-surface protein that is present at high levels in several of the aforementioned aggressive human cancers.

After the APC is bound to cancerous cells, near-infrared (NIR) light is applied either externally or internally, in the case of surgery, to the site where the cancerous cells are disposed. NIR light penetrates living tissue without causing damage. The application of NIR light causes the cancerous cells to undergo necrosis, rapid cell death. Specifically, light irradiation causes the cancerous cells which are bound to the APC to swell with water and increase in internal pressure. The increased internal cellular pressure causes the cancerous cells to burst and die.

Once the cancerous cells burst, they release their contents into extracellular space. The healthy immune system detects this cellular debris as "foreign," resulting in activation of an immune response that further aids in destroying the cancer. Specifically, T lymphocyte and thymocyte cells ("T cells"), a type of white blood cells, attack and destroy the cellular debris. FIGS. 1 and 2 illustrate the mechanism model of the anticancerous effect of NIR-PIT treatment.

One advantage of NIR-PIT therapy is that favorable cells such as immune cells, vascular cells, tissue stem cells, etc., are not damaged because healthy cells are not targeted by the antibody. Thus, the APC does not target the healthy cells.

Presently, phase I and II clinical trials using NIR-PIT are being conducted.

In the early phase of the phase I clinical trial, patients with end-stage head and neck cancers were being treated with the minimum dose of drugs and an amount of light expected to obtain therapeutic effect via NIR-PIT. This therapy has been able to cure most of the patients, including complete recovery (no relapse), and the remaining patients displaying cancer cell reduction of 70% or greater. These patients in the clinical trial were unresponsive to surgery, chemotherapy, or radiation therapy, making their treatment problematic, but through NIR-PIT they were able to achieve the outcomes previously described.

However, despite the above advances, because NIR-PIT is a new cancer treatment, there are many aspects of NIR-PIT treatment that are not yet known. Further, since there is a risk of a patient entering shock if too large a quantity of cancerous cells are destroyed in a single treatment, further research on the efficiency of NIR-PIT treatment is required.

The present disclosure has been developed in light of the above, and presents, in certain embodiments, a means and apparatus for testing the efficiency and effectiveness of NIR-PIT treatments.

SUMMARY

According to an aspect of the disclosure, a method for testing efficiency and effectiveness of a near infrared photo-immunotherapy treatment may comprise: injecting an antibody photosensitizer conjugate (APC) into a patient, applying radiation to the patient, thereby causing the APC to release a ligand, which is excreted in the patient's urine, detecting the presence of the ligand with liquid chromatography-mass spectrometry, measuring, and quantifying an amount of the ligand present in the patient's urine based on analytical results of the liquid chromatography-mass spectrometry. Further the method includes determining the effectiveness of the near infrared photo-immunotherapy treatment based on the measured quantified amount of the ligand present in the patient's urine so as to determine an amount of APC remaining in the patient.

According to an aspect of the disclosure, in the previously described method, the antibody of the APC may be a peptide, a small molecule, as well as combinations thereof. For example, the antibody of the APC may be Cetuximab, Panitumumab, Zalutumumab, Nimotuzumab, Matuzumab, Trastuzumab, Pertuzumab, Rituximab, Daclizumab, J591 or an antigen binding fragment thereof.

According to an aspect of the disclosure, in the previously described method, the photosensitizer of the APC may be an amphiphilic molecule, which comprises a hydrophobic dye skeleton attached to hydrophilic group.

According to an aspect of the disclosure, in the previously described method, the photosensitizer of the APC may comprise a hydrophobic dye.

According to an aspect of the disclosure, in the previously described method, the radiation applied to the patient may be near-infrared light.

According to an aspect of the disclosure, in the previously described method, the radiation applied to the patient may have a wavelength of 660 to 740 nm.

According to an aspect of the disclosure, in the previously described method, the ligand to be released may be a $C_{14}H_{33}NO_{10}S_3Si$ fragment.

According to an aspect of the disclosure, in the previously described method, the liquid chromatography-mass spectrometry may include using a Triple Quadrupole Mass Spectrometer, a Probe Electro Spray Ionization Mass Spectrometer (PESI-MS), a Direct Analysis in Real Time Mass Spectrometer (DART-MS), or an Atmospheric Pressure Solid Analysis Probe Mass Spectrometer (ASAP-MS).

According to an aspect of the disclosure, a near infrared photo-immunotherapy treatment may comprise injecting a first amount of an antibody photosensitizer conjugate (APC) into a patient, applying radiation to the patient, thereby causing the first amount of the APC to release a ligand, which is excreted in the patient's urine, detecting the presence of the ligand with liquid chromatography-mass spectrometry, measuring and quantifying an amount of the ligand present in the patient's urine based on analytical results of the liquid chromatography-mass spectrometry, determining the effectiveness of the near infrared photo-immunotherapy treatment based on the measured quantified amount of the ligand present in the patient's urine so as to determine a portion of the first amount of the APC remaining in the patient, injecting a second amount of the APC into the patient, the second amount being determined based on the portion of the first amount of the APC remaining in the patient, and applying radiation to the patient, thereby causing the second amount of the APC to release a ligand, which is excreted in the patient's urine.

According to an aspect of the disclosure, in the previously described method, the antibody of the APC may be a peptide, a small molecule, as well as combinations thereof. For example, the antibody of the APC may be Cetuximab, Panitumumab, Zalutumumab, Nimotuzumab, Matuzumab, Trastuzumab, Pertuzumab, Rituximab, Daclizumab, J591 or an antigen binding fragment thereof.

According to an aspect of the disclosure, in the previously described treatment, the photosensitizer of the APC may be an amphiphilic molecule, which comprises a hydrophobic dye skeleton attached to hydrophilic group.

According to an aspect of the disclosure, in the previously described treatment, the photosensitizer of the APC may comprise a hydrophobic dye.

According to an aspect of the disclosure, in the previously described treatment, the radiation applied to the patient may be near-infrared light.

According to an aspect of the disclosure, in the previously described method, the radiation applied to the patient may have a wavelength of 660 to 740 nm.

According to an aspect of the disclosure, in the previously described method, the ligand to be released may be a C14H33NO10S3Si fragment.

According to an aspect of the disclosure, in the previously described treatment, the liquid chromatography-mass spectrometry may include using a Triple Quadrupole Mass Spectrometer, a Probe Electro Spray Ionization Mass Spectrometer (PESI-MS), a Direct Analysis in Real Time Mass Spectrometer (DART-MS), or an Atmospheric Pressure Solid Analysis Probe Mass Spectrometer (ASAP-MS).

While the afore-described methods, treatments, and devices have been described individually, these descriptions are not intended to suggest any limitation as to the scope of use or functionality thereof. Indeed these methods, treatments, and devices may be combined in other aspects of the disclosure.

BRIEF DESCRIPTION OF THE DRAWINGS

Further features, the nature, and various advantages of the disclosed subject matter will be more apparent from the following detailed description and the accompanying drawings in which:

FIG. 5 is a table illustrating analysis conditions of an NIT-PIT treatment in accordance with an embodiment;

DETAILED DESCRIPTION

Figure 1:
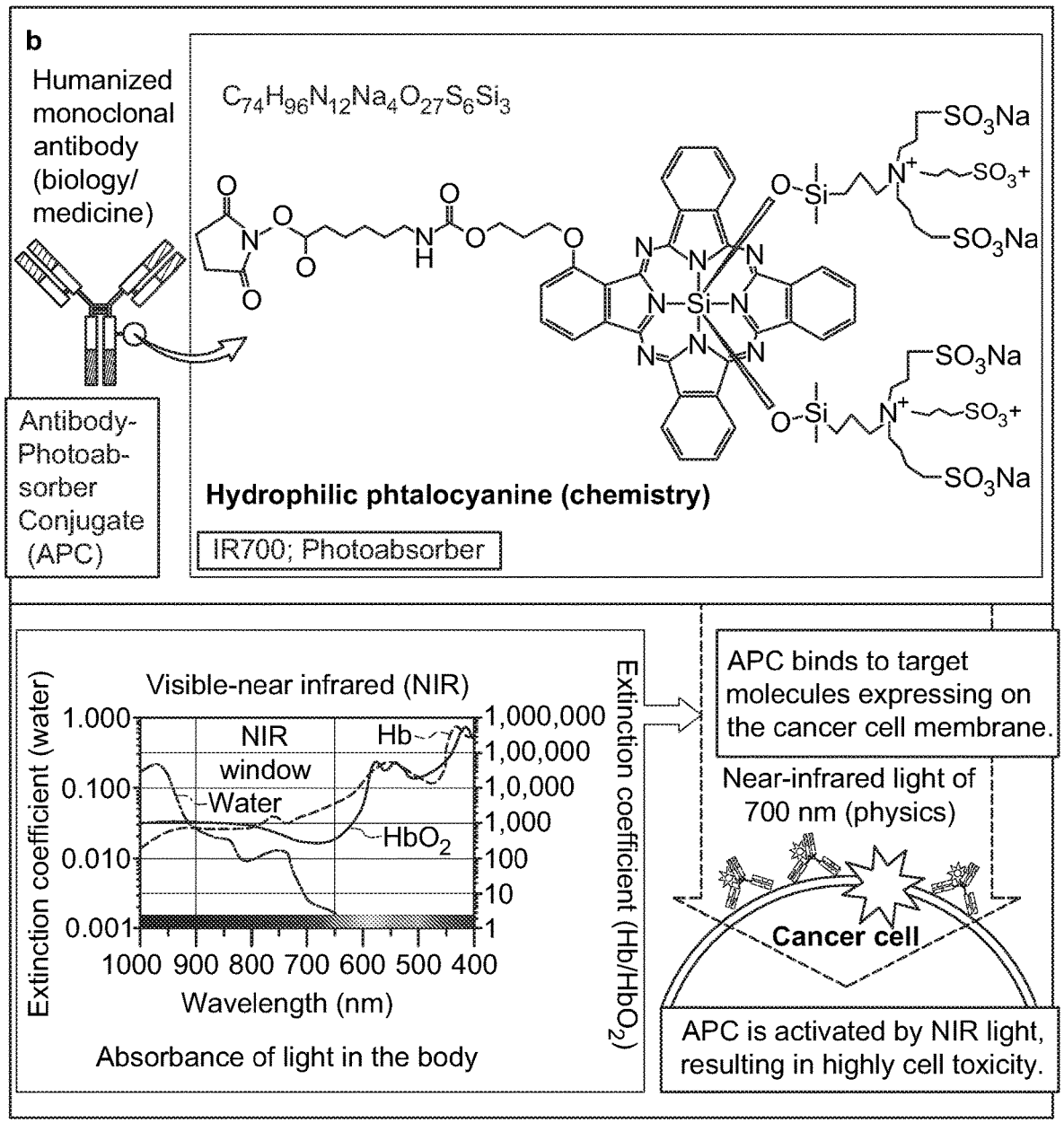
FIG. 1 is a diagram of an NIR-PIT treatment in accordance with an embodiment.
Figure 2:
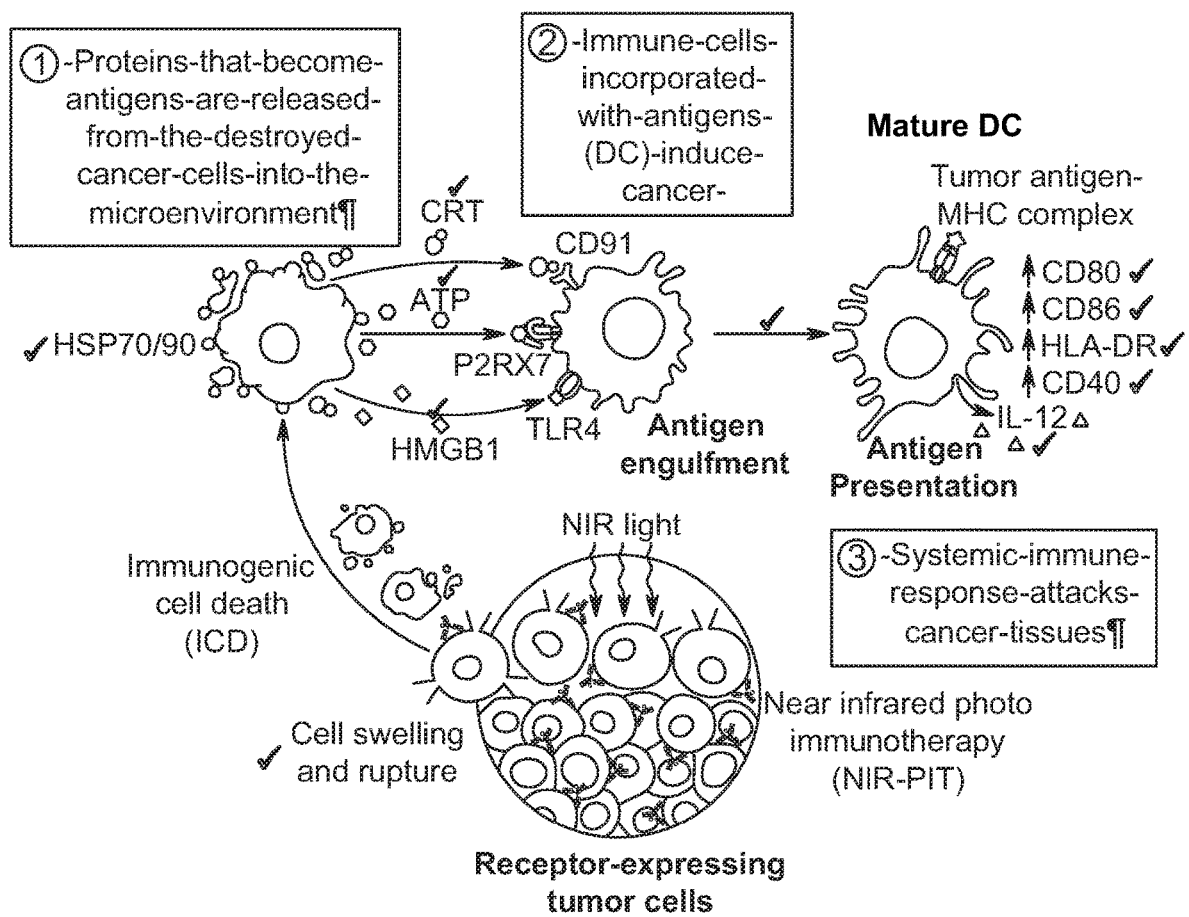
FIG. 2 is a diagram of immunity induction and tumor shrinkage by an NIR-PIT treatment in accordance with an embodiment.

The inventors studied how targeted cancer cells are killed and finally confirmed through several experiments that performing NIR-PIT changes the characteristics of the photosensitizer of the APC.

In NIR-PIT, an antibody may be joined to a photoabsorber/photosensitizer to make an antibody photosensitizer conjugate (APC) and the APC may be injected into a patient. The APC may travel to the tumor cells and bind to the cell(s) selectively.

The antibody of the APC may be designed to target and bind to an antigen or a protein on the tumor cell-surface. For example, the cell surface protein may be a human epidermal growth factor receptor (HER)1, HER2, HER3, HER4, CD5, CD25, CD52, IL-13R, Lewis Y antigen, melanoma-associated antigen (MAGE)1, MAGE2, MAGE3, MAGE4, cancer antigen 125 (CA-125), tumor-associated glycoprotein 72 (TAG-72), gp100, p97 melanoma antigen, human milk fat globule (HMFG), melanoma antigen recognized by T cells 1 (MART1), B melanoma antigen (BAGE)1, BAGE2, G antigen (GAGE)1, GAGE2, GAGE3, GAGE4, GAGE5, GAGE6, breast cancer-associated DF3 antigen, New York esophageal squamous cell carcinoma 1 (NY-ESO-1), mesothelin, or carcinoembryonic antigen (CEA) For example, the antibody may be Cetuximab, Panitumumab, Zalutumumab, Nimotuzumab, Matuzumab, Trastuzumab, Pertuzumab, Rituximab, Daclizumab, J591 or an antigen binding fragment thereof.

The photoabsorber/photosensitizer may be an amphiphilic molecule, which may comprise a hydrophobic dye skeleton attached to hydrophilic group, and may have a higher extinction coefficient in an NIR wave range. Preferably, the hydrophobic dye may be a phthalocyanine dye, for example IRDye® 700, having the chemical formula $C_{74}H_{96}N_{12}Na_4O_{27}S_6Si_3$. However, it is noted that other phthalocyanine dyes, or other dyes in general may also be used.

The photosensitizer may be an amphiphilic molecule, and application of NIR light may cause the photosensitizer to eliminate a hydrophilic group and to change from hydrophilic to hydrophobic, thus aggregation and/or precipitation of hydrophobic APC may occur.

Irradiation, e.g. via NIR light, of the photosensitizer may cause elimination of the hydrophilic group, thus leaving a fragment (a ligand) having highly a hydrophilic structure. This ligand may be hydrophilic enough to pass through the kidneys and to be excreted into the urine.

Generally, a suitable dose of irradiation following administration of the antibody-IR700 is at least 1 J cm−2 at a wavelength of 660-740 nm, for example, at least 10 J cm−2 at a wavelength of 660-740 nm, at least 50 J cm−2 at a wavelength of 660-740 nm, or at least 100 J cm−2 at a wavelength of 660-740 nm, for example 1 to 500 J cm−2 at a wavelength of 660-740 nm. In some examples the wavelength is 660-710 nm. In specific examples, a suitable dose of irradiation following administration of the antibody-IR700 molecule is at least 1.0 J cm−2 at a wavelength of 680 nm for example, at least 10 J cm−2 at a wavelength of 680 nm, at least 50 J cm−2 at a wavelength of 680 nm, or at least 100 J cm−2 at a wavelength of 680 nm, for example 1 to 500 1.0 J cm−2 at a wavelength of 680 nm.

In one embodiment, application of NIR light may cause the photosensitizer, IRDye® 700DX, to change from hydrophilic to hydrophobic, thus aggregation and/or precipitation of hydrophobic APC may occur.

Figure 3:
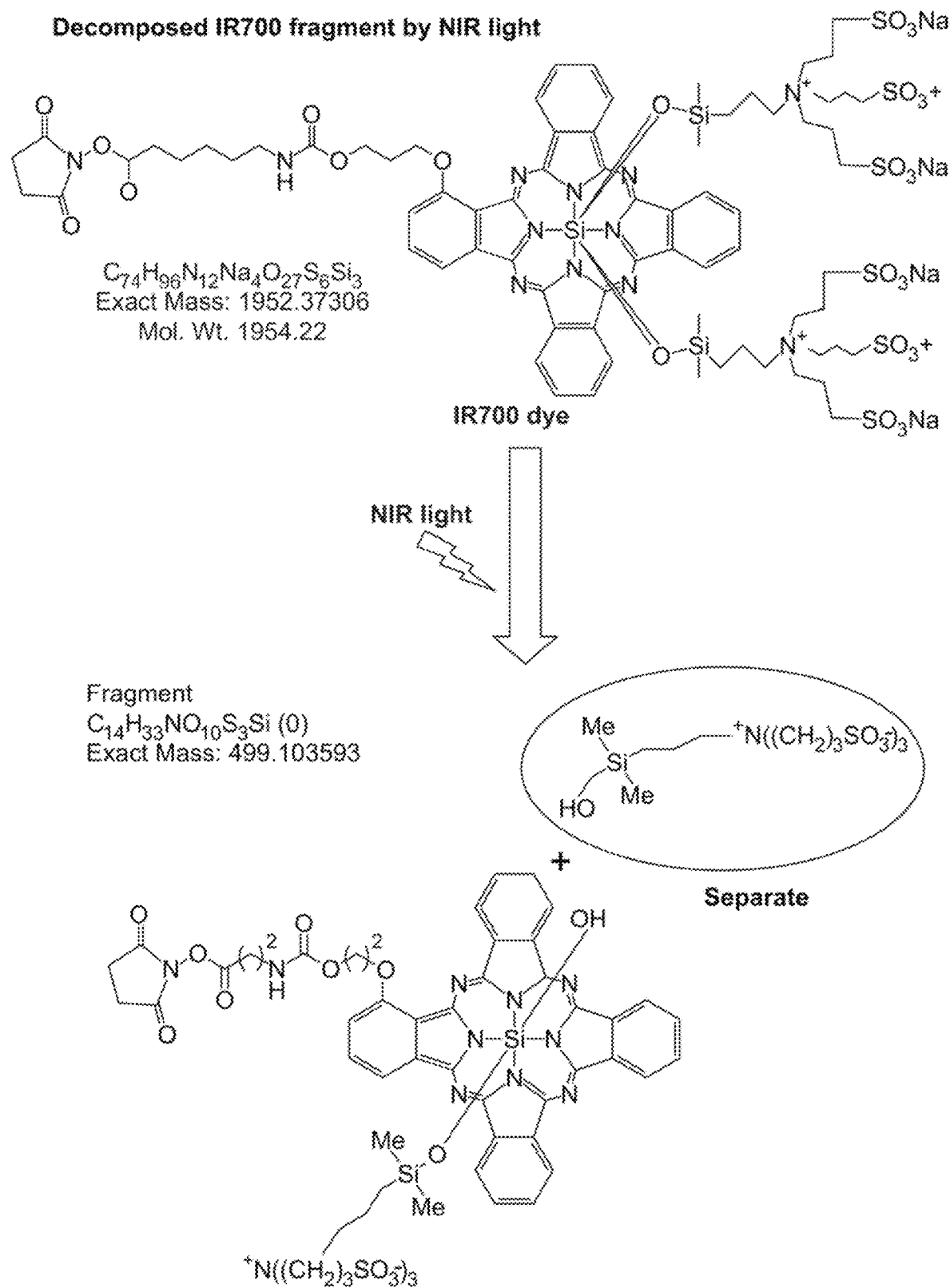
FIG. 3 is a diagram of a chemical reaction of an NIT-PIT treatment in accordance with an embodiment.

Specifically, it is noted that prior to the application of NIR light, the IRDye® 700DX may comprise a highly hydrophobic skeleton attached to two ligands which may increase water solubility of the IRDye® 700DX. Irradiation, e.g. via NIR light, of the IRDye® 700DX may cause a $C_{14}H_{33}NO_{10}S_3Si$ fragment (ligand) to be released from the IRDye® 700DX. This ligand then may pass through the kidneys and be exceeded into the urine. This is illustrated in FIG. 3

Figure 4:
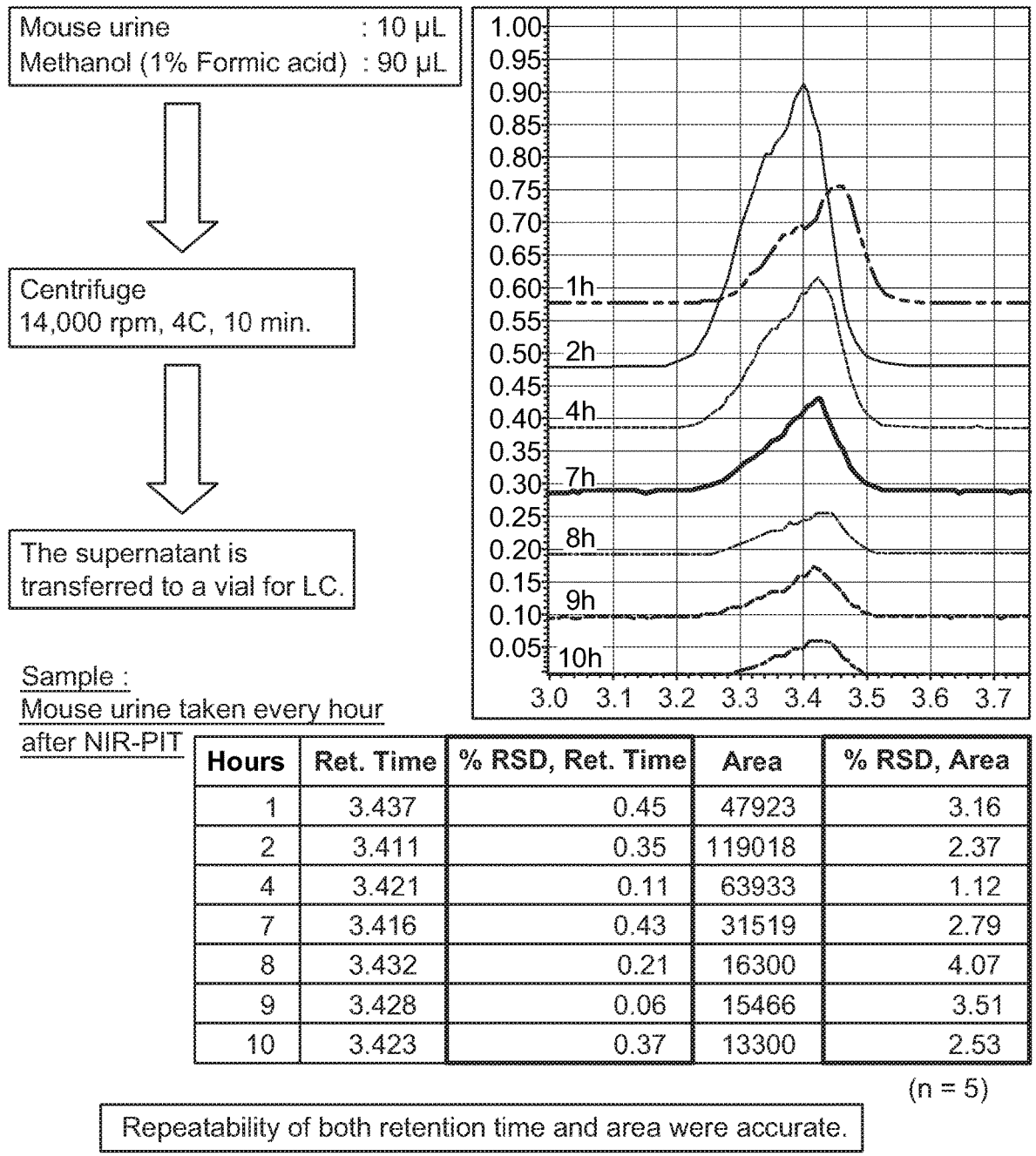
FIG. 4 is an illustration of LCMS detection in accordance with an embodiment.

It has been found that this ligand may be detected, for example, via a conventional LCMS for example, the Nexera LCMS-8050 system (by Shimadzu Corporation). The excreted urine can be mixed with methanol, and spun in a centrifuge. The resulting supernanant may be then run through a conventional LCMS wherein the ligand may be detected, analyzed, and quantized. This is illustrated in FIGS. 4 and 5.

Presently, this ligand detection has been performed to determine the effectiveness and efficiency of NIR-PIT performed on mice, as described below.

In addition, it has also been found that this ligand may also be detected via direct ionization methods using a Probe Electro Spray Ionization Mass Spectrometer (PESI-MS), a Direct Analysis in Real Time Mass Spectrometer (DART-MS), or a Atmospheric Pressure Solid Analysis Probe Mass Spectrometer (ASAP-MS). Further, other related technologies may also be used for determining the ligand amount.

Figure 6:
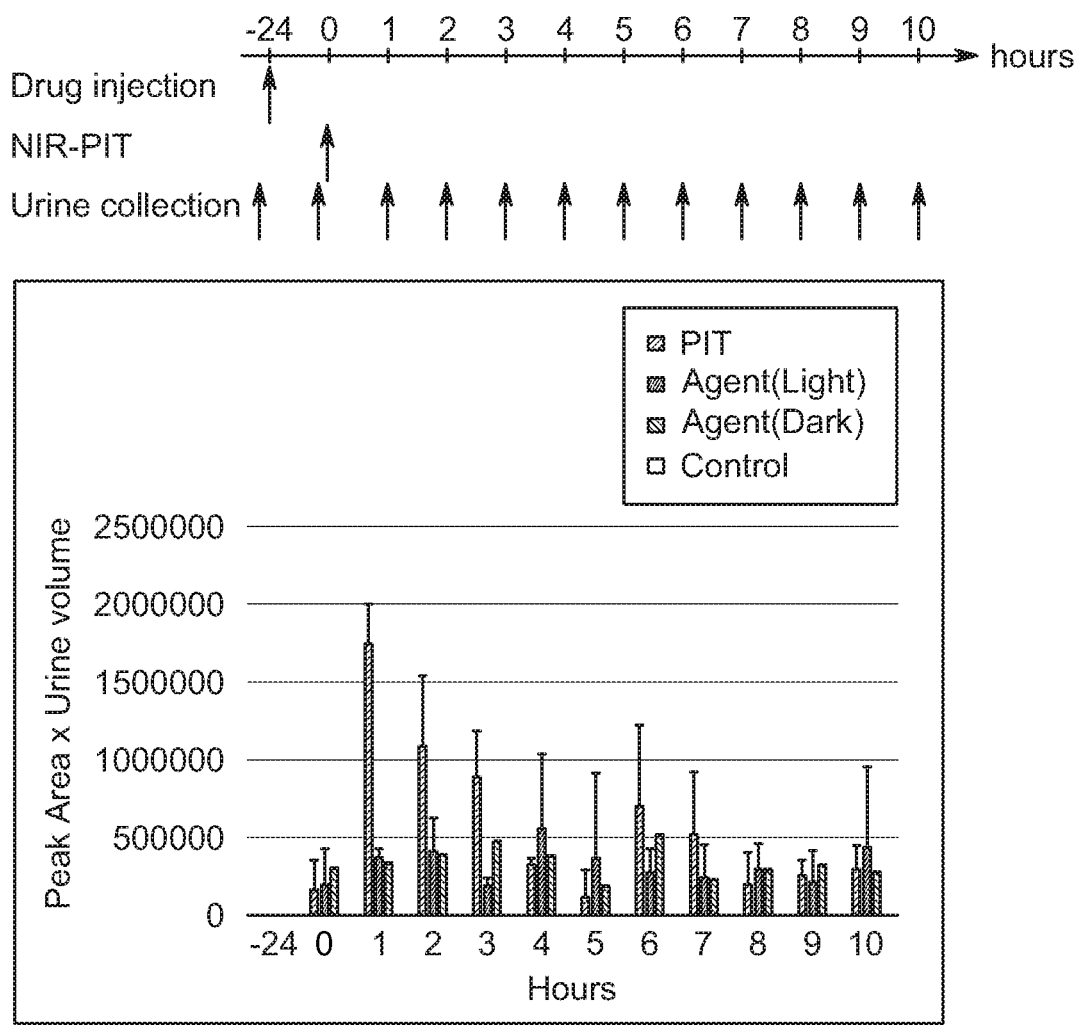
FIG. 6 is a table of drug dispotion in accordance with an embodiment.

Accordingly, since the ligand can be quantitatively measured via LCMS and other methods, the therapeutic effect of NIR-PIT can be evaluated. That is, since the ligand amount is dependent on the number of reacted IR700 molecules, the efficiency of an NIR-PIT treatment can be determined via LCMS. An example of such quantitative measurments is illustrated in FIG. 6.

Currently, ongoing studies are being conducted to improve the analytical method by utilizing different types of inlets to an LCMS for shorter analytical time and easier operation while maintaining sensitivity and accuracy of the array.

Determination of the efficiency of NIR-PIT treatment is important at least because the mechanism of this therapy, as described above, has only recently been discovered. Accordingly, the quantitative results of the measured ligand in excreted urine will provide healthcare professionals with information as to how to proceed with further steps in a treatment involving NIR-PIT.

When treating a relatively large cancerous tumor with NIR-PIT treatments, it is important to not attempt to destroy the relatively large tumor with a single NIR-PIT treatment. Destroying too large an amount of cancerous cells in a single treatment may cause the patient undergoing treatment to enter shock, thus placing them at a significant health risk. In order to avoid such a risk, it is important to target relatively large cancerous tumors with multiple NIR-PIT treatments.

Subsequent NIR-PIT treatments, following the initial NIR-PIT treatment, may occur typically on the next day of the first treatment. However, this time period is not so limited, and may be longer or shorter.

In order to ensure that the appropriate amount of the APC drug is present in the patient's system for an NIR-PIT treatment, the amount of the APC drug remaining after the last NIR-PIT treatment must first be measured. One aspect, as described above, may provide a solution to the problem of measuring the amount of the remaining APC drug in a patient.

Specifically, if a large ligand amount is detected, it can be concluded that the particular NIR-PIT treatment has resulted in activating a correspondingly large amount of the APC. Thus it can be concluded that a correspondingly small amount of the APC drug remains in the patient.

On the other hand, if a small ligand volume is detected, it can be concluded that the particular NIR-PIT treatment has resulted in activating a correspondingly small amount of the APC. Thus it can be concluded that a correspondingly large amount of the APC drug remains in the patient.

The information on the amount of the remaining APC drug in the patient can help a healthcare practitioner determine the correct amount of the APC drug, if required, to be injected into the patient for the subsequent NIR-PIT treatments.

The information gleaned from ligand testing can also be used to develop a treatment plan for individuals undergoing an NIR-PIT treatment. Such a treatment plan may involve the following steps.

First, an appropriate amount of an APC drug, comprising one or more molecules comprising the IRDye® 700DX may be selected and administered to a patient under conditions that allow the one or more molecules comprising the IRDye® 700DX, to bind to their target on a cell surface.

Next, the patient may undergo an NIR-PIT treatment. In the NIR-PIT treatment, the cells whose surfaces have been bound to the one or more molecules comprising the IRDye® 700DX, may be irradiated under conditions that permit killing of the cells, for example via irradiation at a wavelength of 660 to 740 nm at a dose of at least 1 J cm−2. The NIR excitation light wavelength allows penetration of at least several centimeters into tissues. For example, by using fibercoupled laser diodes with diffuser tips, NIR light can be delivered within several centimeters of otherwise inaccessible tumors located deep to the body surface. In addition to treating solid cancers, circulating tumor cells can be targeted since they can be excited when they traverse superficial vessels (for example using an NIR LED wearable devices as disclosed in US 2013/0336995 to Kobayashi et al). The disclosed methods can also be used as a therapy for transplant rejection.

Next, the patient's urine may be analyzed in accordance with the above to detect, and quantize the amount of ligand excreted in the urine.

Next, the information pertaining to the ligand may be analyzed to determine the amount of the APC drug remaining in the patient, and the effectiveness of the previous NIR-PIT treatment.

Next, a subsequent NIR-PIT treatment may be planned, utilizing the information pertaining to the ligand. Next, before the subsequent NIR-PIT treatment is administered, an appropriate amount of the APC drug may be administered to the patient, wherein the appropriate amount is determined based on the information pertaining to the ligand.

Next, the subsequent NIR-PIT treatment may be performed. This process may be repeated as necessary.

While the aforementioned clinical trial is focused on NIR-PIT, in which antibodies are bound to tumor cells, it will soon be possible to use NIR-PIT to target immunosuppressive factors to insure immunity induction. That is, it will soon be possible add different antibodies to the APC to target cancers that express other receptors, such as breast cancer.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof.

The invention claimed is:

1. A method for testing efficiency and effectiveness of a near infrared photoimmunotherapy treatment, the method comprising:
    injecting an antibody photosensitizer conjugate into a patient, wherein the antibody photosensitizer conjugate comprises an antibody conjugated to a $C_{74}H_{96}N_{12}Na_4O_{27}S_6Si_3$ phthalocyanine dye;
    applying radiation to the patient, thereby causing the antibody photosensitizer conjugate to release a $C_{14}H_{33}NO_{10}S_3Si$ ligand, which is excreted in the patient's urine;
    detecting the presence of the $C_{14}H_{33}NO_{10}S_3Si$ ligand with liquid chromatography-mass spectrometry; and
    measuring and quantifying an amount of the $C_{14}H_{33}NO_{10}S_3Si$ ligand present in the patient's urine based on analytical results of the liquid chromatography-mass spectrometry to determine the efficiency and effectiveness of the near infrared photo-immunotherapy treatment,
    wherein the amount of the $C_{14}H_{33}NO_{10}S_3Si$ ligand present in the patient's urine inversely corresponds to an amount of an antibody photosensitizer conjugate remaining in the patient, and
    wherein the amount of the $C_{14}H_{33}NO_{10}S_3Si$ ligand present in the patient's urine positively corresponds with the efficiency and effectiveness of the near infrared photoimmunotherapy treatment.

2. The method according to claim 1, wherein the antibody is Cetuximab, Panitumumab, Zalutumumab, Nimotuzumab, Matuzumab, Trastuzumab, Pertuzumab, Rituximab, Daclizumab, or is an antigen binding fragment thereof.

3. The method according to claim 1, wherein the radiation applied to the patient is near-infrared light.

4. The method according to claim 1, wherein the radiation applied to the patient has a wavelength of 660 to 740 nm.

5. The method according to claim 1, wherein the liquid chromatography-mass spectrometry comprises using a Triple Quadrupole Mass Spectrometer, a Probe Electro Spray Ionization Mass Spectrometer (PESIMS), a Direct Analysis in Real Time Mass Spectrometer (DART-MS), or an Atmospheric Pressure Solid Analysis Probe Mass Spectrometer (ASAP-MS).

6. A near infrared photo-immunotherapy treatment, the treatment comprising:
    injecting a first amount of an antibody photosensitizer conjugate into a patient,
    wherein the antibody photosensitizer conjugate comprises a $C_{74}H_{96}N_{12}Na_4O_{27}S_6Si_3$ phthalocyanine dye;
    applying radiation to the patient, thereby causing the first amount of the antibody photosensitizer conjugate to release a $C_{14}H_{33}NO_{10}S_3Si$ ligand, which is excreted in the patient's urine;
    detecting the presence of the $C_{14}H_{33}NO_{10}S_3Si$ ligand with liquid chromatography-mass spectrometry,
    measuring and quantifying an amount of the $C_{14}H_{33}NO_{10}S_3Si$ ligand present in the patient's urine based on analytical results of the liquid chromatography-mass spectrometry,
    determining the effectiveness of the near infrared photo-immunotherapy treatment based on the measured quantified amount of the $C_{14}H_{33}NO_{10}S_3Si$ ligand present in the patient's urine so as to determine a portion of the first amount of the antibody photosensitizer conjugate remaining in the patient;
    injecting a second amount of the antibody photosensitizer conjugate into the patient, the second amount being determined based on the portion of the first amount of the antibody photosensitizer conjugate remaining in the patient; and
    applying radiation to the patient, thereby causing the second amount of the antibody photosensitizer conjugate to release a $C_{14}H_{33}NO_{10}S_3Si$ ligand, which is excreted in the patient's urine.

7. The treatment according to claim 6, wherein the radiation applied to the patient is near-infrared light.

8. The treatment according to claim 6, wherein the liquid chromatography-mass spectrometry comprises using a Triple Quadrupole Mass Spectrometer, a Probe Electro Spray Ionization Mass Spectrometer (PESI-MS), a Direct Analysis in Real Time Mass Spectrometer (DART-MS), or an Atmospheric Pressure Solid Analysis Probe Mass Spectrometer (ASAP-MS).

* * * * *